(12) United States Patent
Kang et al.

(10) Patent No.: US 9,267,876 B2
(45) Date of Patent: Feb. 23, 2016

(54) DETECTION CELL FOR OPTICAL ANALYSIS OF LIQUID SAMPLE

(75) Inventors: Young Jae Kang, Seoul (KR); Tae Young Kang, Seoul (KR)

(73) Assignee: I-SENS, INC., Seoul (KR)

( * ) Notice: Subject to any disclaimer, the term of this patent is extended or adjusted under 35 U.S.C. 154(b) by 47 days.

(21) Appl. No.: 14/129,092

(22) PCT Filed: Jun. 21, 2012

(86) PCT No.: PCT/KR2012/004922
§ 371 (c)(1),
(2), (4) Date: Dec. 23, 2013

(87) PCT Pub. No.: WO2012/177066
PCT Pub. Date: Dec. 27, 2012

(65) Prior Publication Data
US 2014/0132954 A1    May 15, 2014

(30) Foreign Application Priority Data

Jun. 23, 2011   (KR) .................. 10-2011-0061179

(51) Int. Cl.
*G01N 21/05*   (2006.01)
*G01N 21/03*   (2006.01)

(52) U.S. Cl.
CPC ......... *G01N 21/05* (2013.01); *B01L 2300/0636* (2013.01); *G01N 21/0332* (2013.01); *G01N 2021/0346* (2013.01); *G01N 2021/056* (2013.01); *G01N 2021/058* (2013.01)

(58) Field of Classification Search
CPC ............ G01N 21/05; G01N 2021/056; G01N 2021/052; G01N 2021/058; G01N 21/0332; G01N 2001/1056; G01N 21/03; G01N 2021/0321; G01N 1/28; G01N 1/2813; G01N 2001/002; B01L 2300/0636
USPC ........................................................ 356/246
See application file for complete search history.

(56) References Cited

U.S. PATENT DOCUMENTS 4,233,029 A * 11/1980 Columbus .................. 436/174
4,804,267 A *  2/1989 Greenfield ................. 356/335

(Continued)

FOREIGN PATENT DOCUMENTS

JP   06300720   10/1994
JP   07181178    7/1995

(Continued)

OTHER PUBLICATIONS

International Search Report mailed Jan. 17, 2013 for PCT/KR2012/004922.

*Primary Examiner* — Michael P Lapage
(74) *Attorney, Agent, or Firm* — Lowe Hauptman & Ham, LLP

(57) ABSTRACT

The present invention relates to a cell for optical analysis, wherein a flow space of a low depth is formed by attachment, using a simple double-coated tape without out special processing, of a micro flow channel through which a liquid sample passes, thereby enabling: a very easy manufacturing method; a reduction of manufacturing costs, thereby allowing the cell to be more widely used; a maintenance of a short path length of light with respect to the flow space in which the liquid sample flows, thereby enabling accurate optical analysis without diluting a sample with high absorbance; an expansion of a flow space region along the plane vertical to the light-passing direction, thereby enabling smoother optical analysis and improving the accuracy of optical analysis.

4 Claims, 5 Drawing Sheets

(56) References Cited

U.S. PATENT DOCUMENTS

| | | | | |
|---|---|---|---|---|
| 5,164,598 | A | * | 11/1992 | Hillman et al. ............ 250/341.3 |
| 5,430,542 | A | * | 7/1995 | Shepherd ...................... 356/246 |
| 5,567,617 | A | * | 10/1996 | Caprio et al. .............. 435/287.2 |
| 5,599,503 | A | * | 2/1997 | Manz et al. ................ 422/82.05 |
| 6,084,660 | A | * | 7/2000 | Shartle ........................... 356/39 |
| 6,552,784 | B1 | * | 4/2003 | Dietz et al. ................... 356/246 |
| 8,928,887 | B2 | * | 1/2015 | Popescu et al. ............... 356/450 |
| 2005/0196747 | A1 | * | 9/2005 | Stiene .............................. 435/4 |
| 2010/0307617 | A1 | * | 12/2010 | Miura et al. ............. 137/565.01 |
| 2011/0013183 | A1 | * | 1/2011 | Domaschko et al. ......... 356/246 |
| 2011/0192219 | A1 | * | 8/2011 | Miyamura .................... 73/64.56 |
| 2013/0283931 | A1 | * | 10/2013 | Lochhead et al. ......... 73/861.42 |

FOREIGN PATENT DOCUMENTS

| | | |
|---|---|---|
| JP | 4656149 | 3/2011 |
| KR | 1020010049419 | 6/2001 |
| WO | 2007049332 | 5/2007 |

* cited by examiner

DETECTION CELL FOR OPTICAL ANALYSIS OF LIQUID SAMPLE

CROSS REFERENCE TO RELATED APPLICATION

This application claims the priority of Korean Patent Application No. 10-2011-0061179, filed on Jun. 23, 2011 in the KIPO (Korean Intellectual Property Office). Further, this application is the National Phase application of International Application No. PCT/KR2012/004922 filed Jun. 21, 2012, which designates the United States and was published in Korean.

TECHNICAL FIELD

The present invention relates to a cell for optical analysis, and particularly to, a cell for optical analysis, in which a flow space with a micro thickness is formed by attachment of a simple double-coated tape without any special processing of micro flow channels through which a liquid sample pass so that the cell can be manufactured in a very easy manner, and thus the manufacturing costs can be reduced to allow the cell to be more widely used, in which a path length of light with respect to the flow space in which the liquid sample flows can be maintained shortened to enable accurate optical analysis without diluting a sample with high absorbance, and in which a flow space region can be expanded or changed along the plane perpendicular to a direction in which the light passes through the flow space so that the optical analysis can be performed more smoothly and the accuracy of optical analysis can be improved.

BACKGROUND ART

In general, various experiments or analyses are in progress in a variety of research institutes, school laboratories, hospitals, and the like. Especially, in the biochemical experiment or analysis, an experiment or analysis is conducted using various solutions for analysis of components for various kinds of research data or samples.

As one of these experimental and analytical methods, an optical analysis method is widely used in which light is irradiated onto a liquid sample. Such a optical analysis method is one in which light is irradiated onto the liquid sample using a separate light source, the light having passed through the liquid sample is received and detected by a separate light detector, and the components or characteristics of the liquid sample are calculated through analysis of the detected light.

At this time, the liquid sample is typically provided to a separate transparent cuvette so as to allow the liquid sample to flow into the cuvette, and then light is irradiated onto the liquid sample flowing in a constant flow within the cuvette so that a precise analysis can be performed on the liquid sample. In this case, the cuvette is manufactured in a wide variety of forms depending on the type of the analysis or the liquid sample. The cuvette is constructed of a single cell structure on a disposable basis without an inconvenience of the inner cleaning work so as to perform a simple analysis.

The cuvette is made of a transparent material such as glass or acryl, and includes a flow channel formed therein so as to allow the liquid sample to flow therethrough. In the optical analysis of the liquid sample, light is irradiated onto and penetrates through flow channel in the cuvette to analyze the characteristics of the liquid sample flowing in the flow channel formed. At this time, the inner flow channel of the cuvette is required to be formed such that its vertical distance or thickness is very short in a micro unit along a direction in which the light passes through the flow channel, so that an accurate optical analysis can be performed on the liquid sample with high absorbance owing to a shortened path length of the light passing through the liquid sample.

In other words, in case of a liquid sample with high absorbance, as the path length of the light passing through the liquid sample becomes shorter, an optical analysis can be performed more accurately. Thus, the flow channel of the cuvette has a great effect on accuracy and reliability of the optical analysis of the liquid sample depending on the thickness of the flow channel in which the liquid sample flows in a direction in which the light passes therethrough.

Therefore, the flow channel formed in the cuvette to allow the liquid sample to flow therein is required to be formed very thin in a micro unit, if necessary. However, there occurs a problem in that since it is difficult to make the inner flow channel of the cuvetter very thin, an expensive advanced machining equipment is often needed, which leads to an increase in the manufacturing cost and time. In addition, such a cuvette is not used in small-sized laboratories due to its high price.

DISCLOSURE OF INVENTION

Technical Problem

Accordingly, the present invention has been made to solve the above-mentioned problems occurring in the prior art, and it is an object of the present invention to provide a cell for optical analysis, in which a flow space with a micro thickness is formed by attachment of a simple double-coated tape without any special processing of micro flow channels through which a liquid sample pass so that the cell can be manufactured in a very easy manner, and thus the manufacturing costs can be reduced to allow the cell to be more widely used.

An another object of the present invention is to provide a cell for optical analysis, in which a path length of light with respect to the flow space in which a liquid sample with high absorbance flows can be maintained shortened to enable accurate optical analysis, and simultaneously a flow space region can be expanded or changed along the plane perpendicular to a direction in which the light passes through the flow space so that the optical analysis can be performed more smoothly.

Still another object of the present invention is to provide a cell for optical analysis, in which the flow of a liquid sample is induced to a more stable and uniform state in a flow space in which the liquid sample flows so that the accuracy of the optical analysis can be improved.

Technical Solution

To achieve the above objects, in one aspect, the present invention provides a cell for optical analysis, which is used to irradiate light onto a liquid sample to analyze the liquid sample, the cell including: a double-coated tape including a flow space penetratingly formed at a central portion thereof so as to allow the liquid sample to flow into the flow space; a transparent cuvette configured to be attached to one surface of the double-coated tape, the transparent cuvetter including a main inlet flow channel and a main outlet flow channel formed therein in such a manner as to respectively fluidically communicate with the flow space of the double-coated tape so that the liquid sample can flow into and out of the flow space through the main inlet and outlet flow channels; and a transparent cover configured to be attached to the other surface of the double-coated tape.

In the cell for optical analysis, the transparent cuvette may include an inlet port and an outlet port formed protrudingly outwardly from one side thereof in such a manner as to fluidically communicate with the main inlet flow channel and the main outlet flow channel, respectively.

Also, in the cell for optical analysis, the flow space may be formed such that both edge ends thereof fluidically communicate with the main inlet flow channel and the main outlet flow channel, respectively, and may be formed in a shape which is gradually increased in width as it goes toward the central portion thereof from the both edge ends thereof, which fluidically communicate with the main inlet flow channel and the main outlet flow channel, respectively.

In addition, in the cell for optical analysis, the transparent cuvette may include a micro inlet flow channel and a micro outlet flow channel formed on a surface thereof, which is in close contact with the one surface the double-coated tape, in such a manner as to respectively fluidically communicate with the flow space of the double-coated tape, each of the micro inlet flow channel and the micro outlet flow channel has a diameter smaller than that of each of the main inlet flow channel and the main outlet flow channel, and the main inlet flow channel and the main outlet flow channel fluidically communicate with the flow space through the micro inlet flow channel and the micro outlet flow channel, respectively.

Besides, in the cell for optical analysis, a thermally conductive plate jay be joined to an outer surface of the transparent cuvette and an outer surface of the transparent cover, respectively, the thermally conductive plate having a through-hole formed at a central portion thereof in such a manner as to be positioned above the flow space so that light can pass through the through-hole.

Advantageous Effects

According to the cell for optical analysis of the present invention as constructed above have the following advantages.

A through-hole is penetratingly formed in a simple double-coated tape with a very thin micro thickness, and a flow space of a micro thickness through which a liquid sample can pass is formed in the simple double-coated tape by attachment of a transparent cuvette and a transparent cover to both surface of the adhesive tape so that the cell can be manufactured in a very easy manner without any special processing of micro flow channels.

In addition, the application of a simple double-coated tape with a micro thickness can maintain a shortened path length of light with respect to the flow space in which the liquid sample flows so that the accurate optical analysis of a sample with high absorbance can be performed. Simultaneously, a flow space region can be expanded along the plane perpendicular to a direction in which the light passes through the flow space so that the optical analysis can be performed more smoothly.

Besides, the flow space region can be expanded freely in a state in which the path length of light is maintained uniformly so that the flow of the liquid sample can be induced to a more stable or uniform state, thereby further improving the accuracy of the optical analysis.

EXPLANATION ON SYMBOLS

Figure 1:
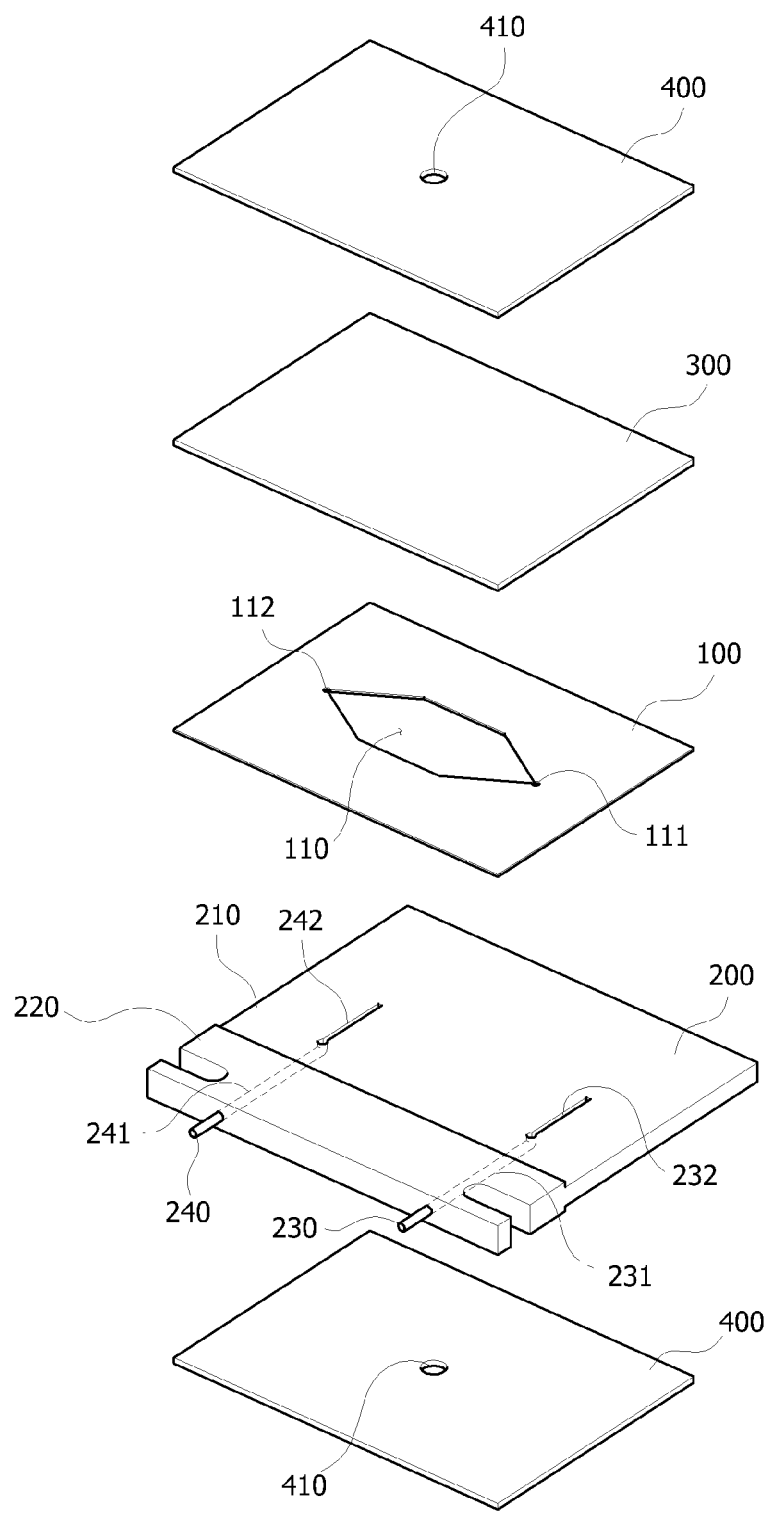
FIG. 1 is a schematic exploded perspective view illustrating a configuration of a cell for optical analysis according to an embodiment of the present invention.

100: double-coated tape
110: flow space
200: transparent cuvette
231: main inlet flow channel
241: main outlet flow channel
232: micro inlet flow channel
242: micro outlet flow channel
300: transparent cover
400: thermally conductive plate

BEST MODE FOR CARRYING OUT THE INVENTION

Now, preferred embodiments of the present invention will be described hereinafter in detail with reference to the accompanying drawings. It should be noted that the same elements in the drawings are denoted by the same reference numerals although shown in different figures. In the following description, the detailed description on known function and constructions unnecessarily obscuring the subject matter of the present invention will be avoided hereinafter.

Figure 2:
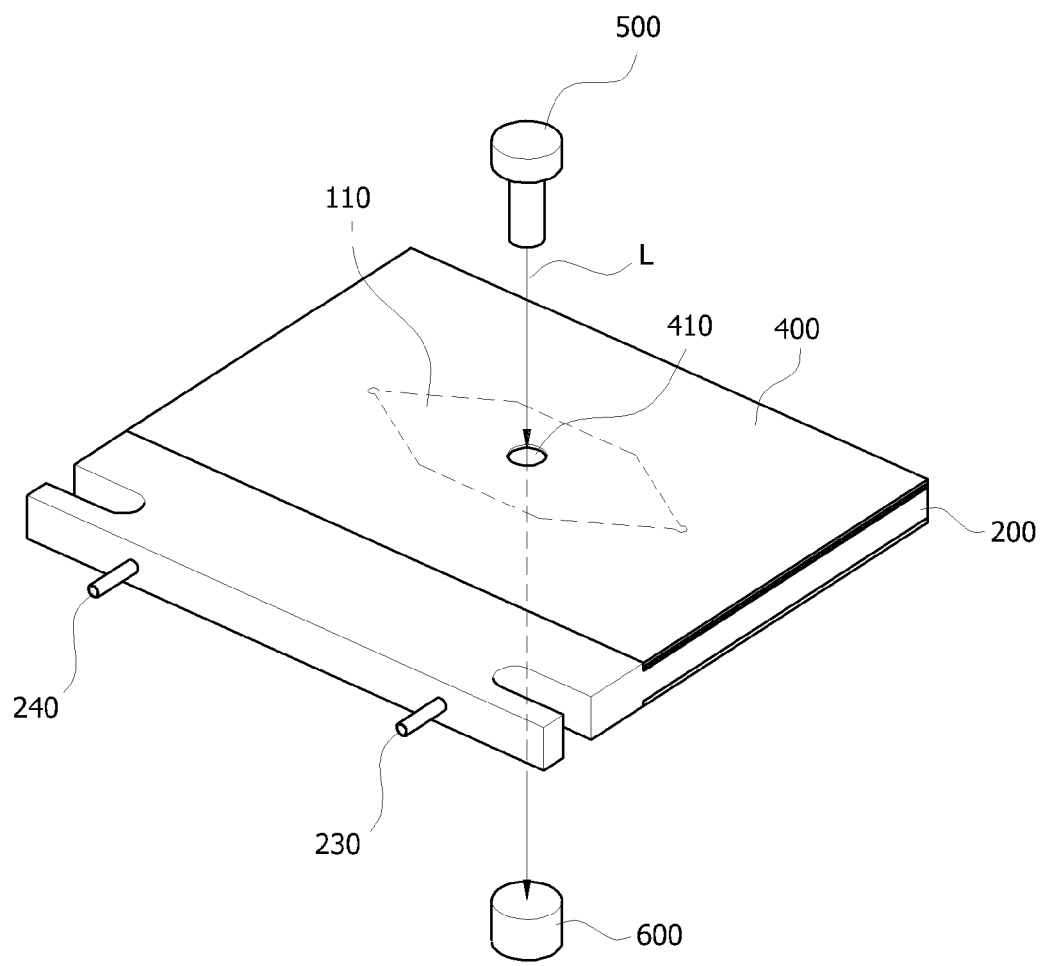
FIG. 2 is a schematic assembled perspective view illustrating a configuration of a cell for optical analysis according to an embodiment of the present invention.
Figure 3:
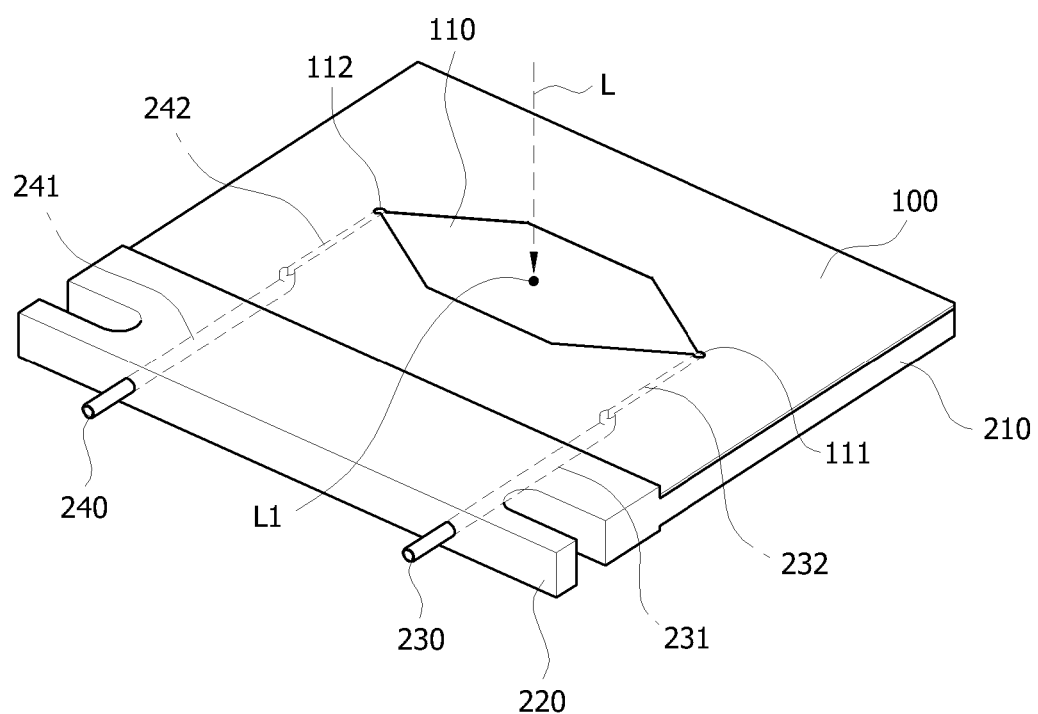
FIG. 3 is a schematic perspective view illustrating a structure of the internal flow channels in a configuration in which a transparent cuvette and a double-coated tape of a cell for optical analysis according to an embodiment of the present invention are joined to each other.

FIG. 1 is a schematic exploded perspective view illustrating a configuration of a cell for optical analysis according to an embodiment of the present invention, FIG. 2 is a schematic assembled perspective view illustrating a configuration of a cell for optical analysis according to an embodiment of the present invention, and FIG. 3 is a schematic perspective view illustrating a structure of the internal flow channels in a configuration in which a transparent cuvette and a double-coated tape of a cell for optical analysis according to an embodiment of the present invention are joined to each other.

A cell for optical analysis according to an embodiment of the present invention is used in an optical analysis method in which light is irradiated onto a liquid sample to analyze the components or characteristics of the liquid sample. The cell for optical analysis can be manufactured in a relatively very simple and easy manner using a double-coated tape. The cell for optical analysis includes a double-coated tape 100, a transparent cuvette 200, and a transparent cover 300.

The double-coated tape 100 is a general tape that has an adhesive coated on both surfaces thereof so as to allow the adhesive both surfaces to all adhere to both adherends. The double-coated tape 100 may be made of a transparent material or an opaque material. The double-coated tape 100 includes a flow space 110 penetratingly formed at a central portion thereof so as to allow a liquid sample to flow into the flow space. Thus, light can pass through the flow space 110 in a thickness direction of the double-coated tape 100.

The transparent cuvette 200 is made of a transparent material such as glass or acryl so as to allow light to pass therethrough, and is attached to one surface of the double-coated tape 100. The transparent cuvette 200 includes a main inlet flow channel 231 and a main outlet flow channel 241 formed therein in such a manner as to respectively fluidically communicate with the flow space 110 of the double-coated tape 100 so that the liquid sample can flow into and out of the flow space 110 through the main inlet and outlet flow channels. The transparent cuvette 200 may be configured to include a cuvette main body 210 that is attached to the double-coated tape 100 and a cuvetter connection part 220 that is formed extending from one side of the cuvette main body 210 and has a thickness larger than that of the cuvette main body 210.

In this case, the cuvette main body 210 is made of a transparent material so as to allow light to pass therethrough, but may be of an opaque material so as to serve as a hand grip or a support. In addition, the cuvette main body 210 may be configured so as to be detachable coupled to the cuvette connection part 220 in a press-fit manner. By virtue of this configuration, since only the cuvette main body 210 can be replaced with new one so as to form a new transparent cuvette 200, the number of parts discarded after being used can be reduced, and thus the maintenance cost can be reduced to enable a more efficient use thereof.

In the meantime, the transparent cuvette 200 is made of a transparent material so as to allow light to pass therethrough. In this case, the transparent cuvette 200 is manufactured such that a colorant is added thereto in the manufacture process thereof. Thus, the transparent cuvette 200 can function as an optical filter that can selectively reduce light with a specific wavelength.

The transparent cover 300 is also made of a transparent material such as glass or acryl so as to allow light to pass therethrough, and is attached to the other surface of the double-coated tape 100.

By virtue of this configuration, since the transparent cuvette 200 and the transparent cover 300 are attached to both surfaces of the double-coated tape 100, the flow space 110 penetratingly formed in the double-coated tape 100 is completely separated from the outside by the transparent cuvette 200 and the transparent cover 300 to form a hermetically sealed structure.

In other words, the flow space 110 defines a space having a micro thickness corresponding to a thickness of the double-coated tape 100. In this case, since the main inlet flow channel 231 and the main outlet flow channel 241 are formed in the transparent cuvette 200 in such a manner as to respectively fluidically communicate with the flow space 110 of the double-coated tape 100, a liquid sample can be supplied in such a manner as to flow into the transparent cuvette 200 through the main inlet flow channel 231 and then flow out of the transparent cuvette 200 through the main outlet flow channel 241

In the case where an optical analysis is performed using the cell for optical analysis, as shown in FIG. 2, light emitted from a separate light source unit 500 is irradiated onto a liquid sample flowing in the flow space 110 having a micro thickness so that a path length of light passing through the liquid sample is shortened, and thus an accurate optical analysis can be performed on a sample with high absorbance.

Thus, in the cell for optical analysis according to an embodiment of the present invention, a flow space 110 is penetratingly formed in a simple double-coated tape with a very thin micro thickness, and the transparent cuvette 200 and the transparent cover 300 are attached to both surfaces of the double-coated tape 100 to define a flow space 110 with a micro thickness between the transparent cuvette 200 and the transparent cover 300 so as to allow a liquid sample to pass therethrough so that the cell can be manufactured in a very easy manner without any special processing of micro flow channels, unlike the prior art in which the micro flow channels are not formed in the cuvette. In the case where the optical analysis is performed on the liquid sample using the cell for optical analysis, light L irradiated onto the sample from the light source unit 500 is preferably oriented to pass through any point L1 within a flow space 110 region.

More specifically, in the optical analysis of the liquid sample, flow channels with a micro thickness are formed in the transparent cuvette so that a path length of light passing through the liquid sample is shortened as described above, and light is irradiated onto the liquid sample flowing through the flow channels to perform the optical analysis on the liquid sample.

The cell for optical analysis according to an embodiment of the present invention enables the transparent cuvette 200 and the transparent cover 300 to be attached to both surface of the double-coated tape 100 as described above so that the flow space 110 can be defined between the transparent cuvette 200 and the transparent cover 300 in a very simple manner without any coaching process so as to allow the liquid sample to pass therethrough. In this case, since the flow space 110 has the same thickness as that of the double-coated tape 100, a double-coated tape 100 having a very thin thickness in a micro unit is used, if necessary, so that the flow space 110 with a micro thickness can be formed in a very simple manner.

In the case where the optical analysis is performed using the cell for optical analysis, light L is irradiated onto the sample along the thickness direction of the flow space 110 at any point L1 within the flow space 110 region with a micro thickness, which is formed in the double-coated tape 100 so that a path length of the light passing through the liquid sample can be greatly shortened to enable an accurate optical analysis of a sample with high absorbance.

Meanwhile, the main inlet flow channel 231 and the main outlet flow channel 241 are formed in the transparent cuvette 200 so as to allow the liquid sample to flow into and out of the flow space 110 therethrough. The main inlet flow channel 231 and the main outlet flow channel 241 are formed to merely allow the liquid sample to be supplied to the flow space 110, and are not portions to which light is substantially irradiated for optical analysis of the liquid sample. Thus, the main inlet flow channel 231 and the main outlet flow channel 241 need not to have a micro thickness and are preferably formed relatively large in diameter for the sake of easiness of the supply of a sufficient liquid sample and the processing thereof.

Thus, since the main inlet flow channel 231 and the main outlet flow channel 241 need not to be manufactured through a micro machining process, they may be formed through a general and simple manufacture process in such a manner that a groove is machined in an inner space of the transparent cuvette 200 using a general tool such as a drill, or may be formed in such a manner as to be integrally formed with each other in an injection-molding process.

In addition, the transparent cuvette 200 may include an inlet port 230 and an outlet port 240 formed protrudingly outwardly from one side thereof in such a manner as to fluidically communicate with the main inlet flow channel 231 and the main outlet flow channel 241, respectively. This configuration of the inlet port 230 and an outlet port 240 is aimed at supplying the liquid sample to the flow space 110. For example, the liquid sample can be supplied to the transparent cuvette 200 from a separate liquid sample supply unit (not shown) through the inlet port 230, and can be discharged to a separate discharge port (not shown) from the transparent cuvette 200 through the outlet port 240.

Thus, the liquid sample supplied to the transparent cuvette 200 from the outside through the inlet port 230 flows through the main inlet flow channel 231 and then is introduced into the flow space 110 with a micro thickness. Thereafter, the liquid sample introduced into the flow space 110 flows along the flow space 110 toward the main outlet flow channel 241 and then is discharged to the outside from the main outlet flow channel 241 through the outlet port 240. By virtue of this process, the liquid sample continues to circulatingly flow into the flow space 110.

Like this, the main inlet flow channel 231 and the main outlet flow channel 241 may be formed in the transparent cuvette 200 in such a manner as to directly fluidically communicate with the flow space 110 of the double-coated tape 100, but a micro inlet flow channel 232 and a micro outlet flow channel 242 may be formed on a surface of the transparent cuvette 200, which is in close contact with the one surface the double-coated tape 100, in such a manner as to respectively fluidically communicate with the flow space 110 of the double-coated tape 100 as shown FIGS. 1 and 3.

In other words, the micro inlet flow channel 232 and the micro outlet flow channel 242 formed on the surface of the transparent cuvette 200 may be respectively connected at one ends to the main inlet flow channel 231 and the main outlet flow channel 241 formed in the transparent cuvette 200 so as to fluidically communicate with the main inlet flow channel 231 and the main outlet flow channel 241, and may be respectively connected at the other ends to the flow space 110 of the double-coated tape 100 so as to fluidically communicate the flow space 110, so that the main inlet flow channel 231 and the main outlet flow channel 241 can fluidically communicate with the flow space 110 through the micro inlet flow channel 232 and the micro outlet flow channel 242. In this case, each of the micro inlet flow channel 232 and the micro outlet flow channel 242 is preferably formed to have a diameter smaller than that of each of the main inlet flow channel 231 and the main outlet flow channel 241.

Therefore, the liquid sample introduced into the transparent cuvette 200 through the inlet port 230 flows along the main inlet flow channel 231 toward the micro inlet flow channel 232, and then flows into the flow space 110 from the micro inlet flow channel 232. In addition, the liquid sample having flown into the flow space 110 flows out of the flow space 110 toward the micro outlet flow channel 242, and then is discharged to the outside through the outlet port 240 via the micro outlet flow channel 242.

Like this, the micro inlet flow channel 232 is formed between the main inlet flow channel 231 and the flow space 110 so that the flow of the liquid sample flowing into the flow space 110 with a relatively small micro thickness from the main inlet flow channel 231 with a relatively large diameter can be maintained in a more stable state.

In other words, the main inlet flow channel 231 is formed relatively large in diameter as described above, and the flow space 110 is formed relatively very small in thickness compared to the diameter of the main inlet flow channel 231. For this reason, when the liquid sample directly flows into the flow space 110 from the main inlet flow channel 231, a difference of a flow pressure may be caused by a difference between the diameter of the main inlet flow channel 231 and the thickness of the flow space 110, leading to instability of the flow of the liquid sample flowing into the flow space 110. The flow of the liquid sample is required to be maintained stably in the flow space 110, i.e., a region to which light is irradiated in order to enable a more accurate optical analysis. Thus, according to an embodiment the present invention, the micro inlet flow channel 232 having a diameter smaller than that of the main inlet flow channel 231 is formed on the surface of the transparent cuvette 200 and the liquid sample flows into the flow space 110 from the micro inlet flow channel 232 so that an unstable flow of the liquid sample can be alleviated.

In other words, the unstable flow of the liquid sample occurring due to a difference between the diameter of the main inlet flow channel 231 and the thickness of the flow space 110 is alleviated through the micro inlet flow channel 232 so that the flow of the liquid sample flowing into the flow space 110 can be made further stable, thereby enabling a more accurate optical analysis.

Although only the micro inlet flow channel 232 has been described, the operation principle of the micro outlet flow channel 242 also is the same as that of the micro inlet flow channel 232. The micro outlet flow channel 242 interposed between the flow space 110 and the main outlet flow channel 241 can alleviate the unstable flow of the liquid sample flowing out of the flow space 110.

In the meantime, a thermally conductive plate 400 is joined to an outer surface of the transparent cuvette 200 and an outer surface of the transparent cover 300, respectively, and has a through-hole 410 formed at a central portion thereof in such a manner as to be positioned above the flow space 110 of the double-coated tape 100 so that light can pass through the through-hole 410.

Since the thermally conductive plate 400 may be formed of an opaque material such as aluminum that has an excellent heat conductivity and is lightweight, the through-hole 410 is formed at the central portion of the thermally conductive plate 400 in such a manner as to be positioned above the flow space 110 of the double-coated tape 100 so that the light can be irradiated onto the flow space 110 of the double-coated tape 100.

Like this, the thermally conductive plate 400 is joined to the transparent cuvette 200 and the transparent cover 300 to transfer heat to the interior of the cell for optical analysis so that the liquid sample flowing through the inner flow channels of the transparent cuvette 200 can be maintained under a specific temperature condition.

For example, in the case where the liquid sample is blood and an optical analysis is performed on the blood, the flow state of the blood is required to be maintained under an environmental condition maximally close to the human body so that a more accurate analysis result of the blood can be obtained. Thus, the temperature of the blood flowing in the flow space 110 is preferably maintained at 37.5° similar to the normal temperature of the human body. Herein, the separate thermally conductive plate 400 is joined to the outer surfaces of the transparent cuvette 200 and the transparent cover 300 so that the internal temperature of the cell for optical analysis can be maintained constantly. For example, the thermally conductive plate 400 may be heated by being exposed to hot water or light so that the internal temperature of the cell for optical analysis can be risen and maintained at this temperature.

The thermally conductive plate 400 also performs a function that can maintain the interior of the cell for optical analysis at a constant temperature as well as can protect the interior of the cell for optical analysis from a physical damage such as an external shock.

Hereinafter, the shape of the flow space 110 formed in the double-coated tape 100 will be described with reference to FIGS. 4 and 5.

Figure 4:
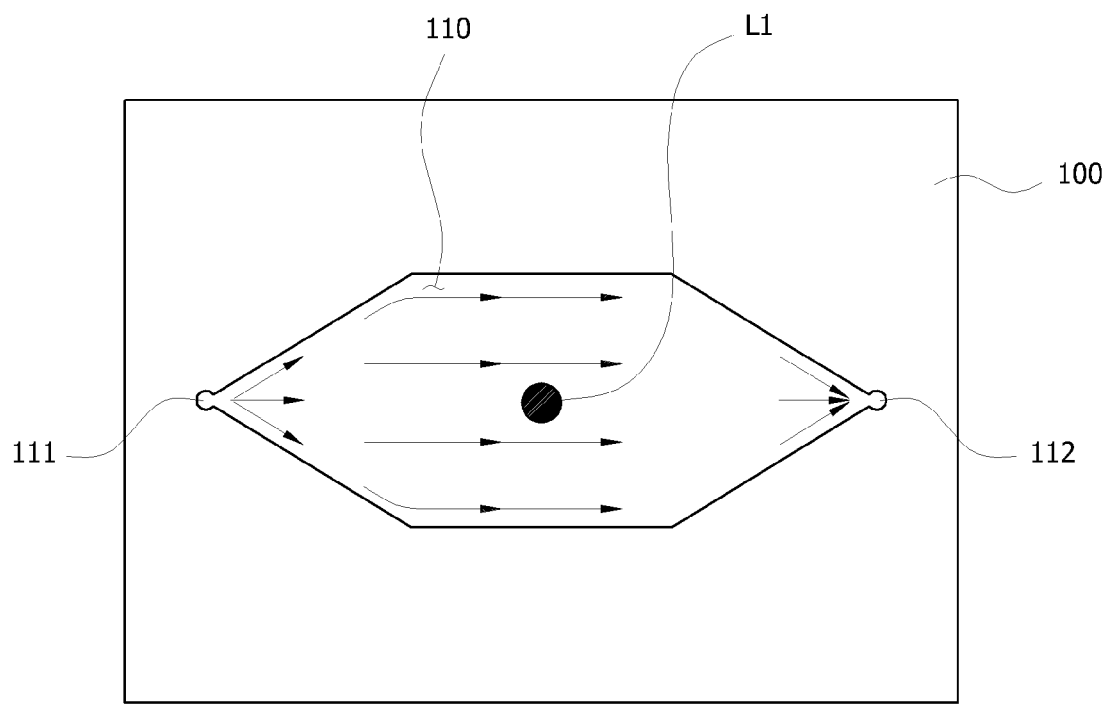
FIG. 4 is a conceptual view illustrating the flow of a liquid sample in a flow space formed in a double-coated tape of a cell for optical analysis according to an embodiment of the present invention.
Figure 5:
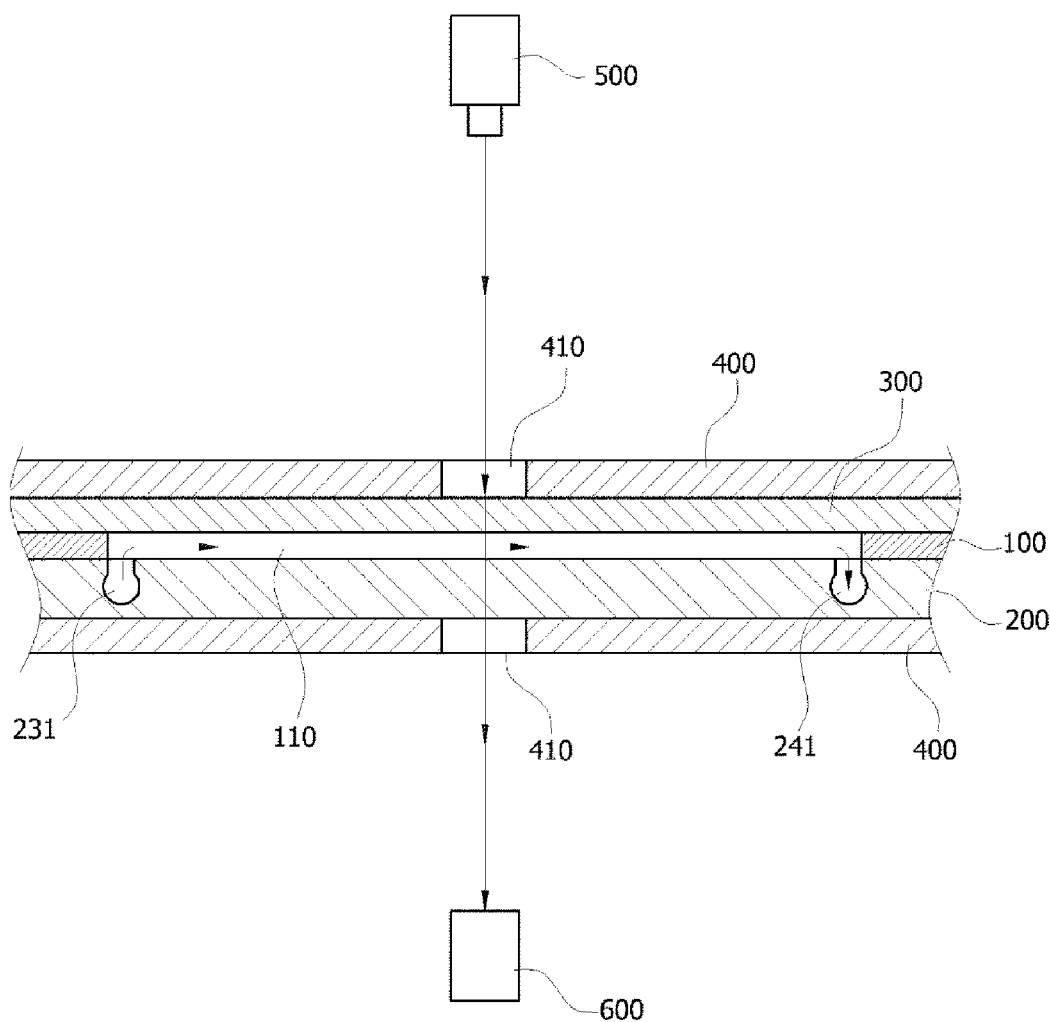
FIG. 5 is a schematic cross-sectional view illustrating an internal structure of a cell for optical analysis according to an embodiment of the present invention.

FIG. 4 is a conceptual view illustrating the flow of a liquid sample in a flow space formed in a double-coated tape of a cell for optical analysis according to an embodiment of the present invention, and FIG. 5 is a schematic cross-sectional view illustrating an internal structure of a cell for optical analysis according to an embodiment of the present invention.

As shown in FIGS. 1 and 3, the flow space 110 of the double-coated tape 100 is formed such that both edge ends 111 and 112 thereof fluidically communicate with the main inlet flow channel 231 and the main outlet flow channel 232, respectively. The flow space 110 may be formed in a lengthily extending simple shape with the same width.

However, the flow space 110 according to the present invention is formed in a shape which is gradually increased in width as it goes toward the central portion thereof from the both edge ends thereof, which fluidically communicate with the main inlet flow channel 231 and the main outlet flow channel 241, respectively, as shown FIGS. 1, 3 and 4. By virtue of this configuration, the flow of the liquid sample can be induced to a more uniform state, and an irradiation region of light by the light source unit 500 can be extended, thereby enabling an easier optical analysis of the liquid sample.

More specifically, in the optical analysis of the liquid sample, as shown in FIG. 2, light L emitted from the separate light source unit 500 is irradiated onto a liquid sample, the light having passed through the liquid sample is received and detected by a separate light detector 600, and characteristics of the liquid sample are analyzed through analysis of the detected light. At this time, the light L emitted from the light source unit 500 passes through any point L1 within the flow space 110 region as described above. In this case, since the flow space 110 is formed in a shape which is widened at the central portion thereof, it is easy to allow the light emitted from the light source unit 500 to be oriented so as to pass through any point within the flow space 110 region, and thus the optical analysis can be performed in a smoother and more accurate manner.

The flow space 110 according to an embodiment of the present invention is not changed in thickness in terms of its structure although it is widened at the central portion thereof, and thus the path length of the light passing through the liquid sample is not increased. Hence, the optical analysis can be easily performed on the sample without a degradation of the accuracy of the optical analysis.

Moreover, since the flow space 110 having such a shape is gradually increased in width as it goes toward the central portion thereof from the both edge ends 111 and 112 thereof, the liquid sample flows diffusely toward the central portion of the flow space 110 from one end 111 thereof fluidically communicating with the main inlet flow channel 231 as shown FIG. 4. Thus, various particle components contained in the liquid sample are not agglomerated or mixed with each other, but can be distributed diffusely over a large area of the flow space, i.e., the liquid sample flows distributedly in a more uniform state, thereby enabling a more accurate optical analysis. For example, in the case where the liquid sample is blood, various components such as blood platelet, electrolyte, leucocyte, and hematocyte contained in the blood are not agglomerated or mixed with each other, but can be distributed diffusely over a large area of the flow space, thereby enabling a more accurate optical analysis.

In other words, the cell for optical analysis according to an embodiment of the present invention enables the flow space 110 of the double-coated tape 100 to be formed to have a micro thickness in a direction in which light passes through the flow space so that the path length of light can be maintained shortened, thereby enabling an accurate optical analysis to be performed on a sample with high absorbance. Simultaneously, the flow space 110 region can be expanded along the plane perpendicular to a direction in which the light passes through the flow space so that the optical analysis can be performed more smoothly as well as the accuracy of optical analysis can be further improved by inducing the liquid sample to a more uniform flow state.

In the meantime, although it has been described that the flow space 110 is formed in a shape which is gradually increased in width as it goes toward the central portion thereof from the both edge ends 111 and 112 thereof, the flow space 110 may be modified in various geometrical shapes which can change the flow of a sample in the flow space 110 such as being formed in a straight shape or a bent shape depending on the need of a user.

While the present invention has been described in connection with the exemplary embodiments illustrated in the drawings, they are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

The invention claimed is:

1. A cell for optical analysis of a liquid sample by irradiating light onto the liquid sample, the cell comprising:
a double-coated tape including a flow space penetratingly disposed at a central portion of the double-coated tape, to allow the liquid sample to flow into the flow space;
a transparent cuvette configured to be attached to a first surface of the double-coated tape, and including a main inlet flow channel and a main outlet flow channel,
wherein the main inlet flow channel and main outlet flow channel are configured to respectively and fluidically communicate with the flow space of the double-coated tape to enable the liquid sample to flow into and out of the flow space through the main inlet and outlet flow channels; and
a transparent cover configured to be attached to a second surface of the double-coated tape, the second surface opposite the first surface,
wherein the transparent cuvette includes a micro inlet flow channel and a micro outlet flow channel disposed within the transparent cuvette and having a cross-section in the lengthwise direction of the micro intel and outlet flow channels open to the flow space of the double-coated tape for fluidic communication between the micro inlet and outlet flow channels and the flow space, and
wherein the main inlet flow channel and the main outlet flow channel fluidically communicate with the flow space through the micro inlet flow channel and the micro outlet flow channel, respectively.

2. The cell for optical analysis according to claim 1, wherein the transparent cuvette includes an inlet port and an outlet port outwardly protruding from a first side of the transparent cuvette to fluidically communicate with the main inlet flow channel and the main outlet flow channel, respectively, wherein the inlet port and the outlet port connect with the micro inlet flow channel and the micro outlet flow channel, respectively.

3. The cell for optical analysis according to claim 1, wherein the flow space comprises opposite ends which fluidically communicate with the main inlet flow channel and the main outlet flow channel, respectively, and wherein the flow space has a shape which is gradually increased in width toward a central portion of the flow space from the opposite ends of the flow space.

4. The cell for optical analysis according to claim 1, further comprising a thermally conductive plate disposed on an outer surface of the transparent cover, wherein the transparent cover is disposed on the surface of the transparent cuvette, and wherein the thermally conductive plate comprises a through-hole disposed at a central portion of the thermally conductive plate and positioned above the flow space to enable light to pass through the through-hole.

* * * * *